United States Patent
Azhayev et al.

(10) Patent No.: US 7,491,817 B2
(45) Date of Patent: *Feb. 17, 2009

(54) UNIVERSAL SUPPORTS FOR OLIGONUCLEOTIDE SYNTHESIS

(75) Inventors: Alex Azhayev, Siilinjarvi (FI); Maxim Antopolskii, Kuopio (FI)

(73) Assignee: Glen Research Corporation, Sterling, VA (US)

( * ) Notice: Subject to any disclaimer, the term of this patent is extended or adjusted under 35 U.S.C. 154(b) by 389 days.

This patent is subject to a terminal disclaimer.

(21) Appl. No.: 10/851,289

(22) Filed: May 24, 2004

(65) Prior Publication Data

US 2005/0250116 A1    Nov. 10, 2005

Related U.S. Application Data

(63) Continuation of application No. 09/995,785, filed on Nov. 29, 2001, now Pat. No. 6,770,754.

(60) Provisional application No. 60/253,750, filed on Nov. 29, 2000.

(51) Int. Cl.
*C07H 21/00* (2006.01)
*C07C 233/00* (2006.01)

(52) U.S. Cl. ............... 536/25.3; 564/123; 564/152; 564/155; 564/161; 564/192; 564/193; 564/194

(58) Field of Classification Search ............... 536/25.3; 564/123, 152, 155, 161, 192, 193, 194
See application file for complete search history.

(56) References Cited

U.S. PATENT DOCUMENTS

| | | | |
|---|---|---|---|
| 5,681,945 A | 10/1997 | McLean | |
| 5,886,193 A | 3/1999 | McLean | |
| 6,300,070 B1 | 10/2001 | Boles | |
| 6,310,189 B1 | 10/2001 | Fodor | |
| 6,312,894 B1 * | 11/2001 | Hedgpeth et al. | ............... 435/6 |
| 6,316,616 B1 * | 11/2001 | Jacobsen et al. | ............ 540/484 |
| 6,770,754 B2 * | 8/2004 | Azhayev et al. | ............ 536/25.3 |

OTHER PUBLICATIONS

S. Scott, P. Hardy, R.C. Sheppard, and M.J. McLean, "A Universal Support for Oligonucleotide Synthesis," *Innovation and Perspectives in Solid Phase Synthesis*, 3$^{RD}$ International Symposium, 1994, pp. 115-124.

C. Scheuer-Larsen, C. Rosenbohm, T.J.D. Jorgensen, and J. Wengel, "Introduction of a Universal Solid Support for Oligonucleotide Synthesis," *Nucleosides & Nucleotides*, 1997, vol. 16, pp. 67-80.

M.H. Lyttle, D.J. Dick, D. Hudson, and R.M. Cook, "A Phosphate Bound Universal Linker for DNA Synthesis," *Nucleosides & Nucleotides*, 1999, vol. 18, pp. 1809-1824.

A.V. Azhayev, "A New Universal Solid Support for Oligonucleotide Synthesis," *Tetrahedron*, 1999, vol. 55, pp. 787-800.

Vu et al., "Use of Phthaloyl Protecting Group for the Automated Synthesis of 3'-[(Hydroxypropyl)amino] and 3'-[Hydroxypropyl)triglycyl] Oligonucleotide Conjugates", Bioconjugate Chem., 6, pp. 599-607, 1995.

Urata et al., "A Convenient Synthesis of Oligonucleotides with a 3'-Phospho-glycolate and 3'-Phosphoglycaldhyde Terminus", Tetrahedron Letters, vol. 34, No. 25, pp. 4015-4018, 1993.

Kobayashi et al., "A Convenient Synthesis of (E)-4-Alkoxy-2-amino-3-butenoic Acid Derivatives", Bull. Chem. Soc., Japan 72, 2307-2313, 1999.

* cited by examiner

*Primary Examiner*—Mark L Shibuya
(74) *Attorney, Agent, or Firm*—Banner & Witcoff, Ltd.

(57) ABSTRACT

Universal supports for oligonucleotide synthesis include a support material represented by the following formula:

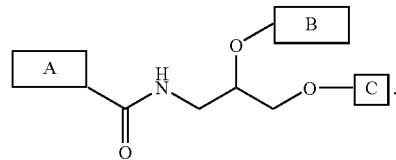

In this formula, substituent A is selected from H, alkyl, aryl, or a polymeric or silica base material; substituent B is selected from acyl, aroyl, or a polymeric or silica base material; and substituent C is selected from a dimethoxytrityl group or a protecting group removable under acidic or neutral conditions. For the supports, one of substituents A or B constitutes the polymeric or silica base material. In use, an oligonucleotide is attached to the support at substituent C.

27 Claims, 5 Drawing Sheets

UNIVERSAL SUPPORTS FOR OLIGONUCLEOTIDE SYNTHESIS

RELATED APPLICATION DATA

This application is a continuation of U.S. patent application Ser. No. 09/995,785, filed Nov. 29, 2001 U.S. Pat. No. 6,770,754, and it further claims priority benefits based on U.S. Provisional Patent Application No. 60/253,750, filed Nov. 29, 2000. These priority application are entirely incorporated herein by reference.

FIELD OF THE INVENTION

The present invention relates to supports used in DNA and RNA synthesis. The supports according to the invention do not include a pre-attached nucleoside, and therefore can be used universally for any DNA or RNA synthesis, irrespective of the desired terminal nucleoside. Moreover, the supports according to the invention allow fast cleavage and dephosphorylation at relatively low temperatures and under relatively mild reaction conditions.

BACKGROUND OF THE INVENTION

A vast majority of oligonucleotide syntheses are carried out on supports to which a first nucleoside has been pre-attached (e.g., by a succinate or hydroquinone-O,O'-diacetate linker). After routine cleavage and deprotection steps, this nucleoside becomes the 3' terminal nucleoside of the target oligonucleotide. For standard DNA and RNA synthesis, this requires an inventory of four deoxynucleoside and four ribonucleoside supports, i.e., a different support depending on the desired terminal nucleoside.

A "universal" solid support (i.e., a support without the first nucleoside attached) for DNA and RNA synthesis that permitted direct coupling of any residue and elimination of the terminal phosphodiester linkage at the same time as the deprotection step would offer several advantages. For example, such a universal support would: (a) eliminate the need for an inventory of several different nucleoside supports; (b) minimize the possibility of error in the selection of the correct support type; (c) reduce the time and eliminate errors in the generation of an array of nucleoside supports in 96 well synthesizers; and (d) allow the preparation of oligonucleotides containing a 3'-terminal nucleoside which is not available as a support.

In spite of these major potential benefits of universal supports, at the present time, the use of universal supports for DNA and RNA synthesis has not been favored. One major hurdle to overcome relates to finding conditions to eliminate the terminal phosphate, produced from the first nucleoside phosphoramidite addition cycle to the required terminal hydroxyl group. This problem is considered in more detail below.

Figure 1A:
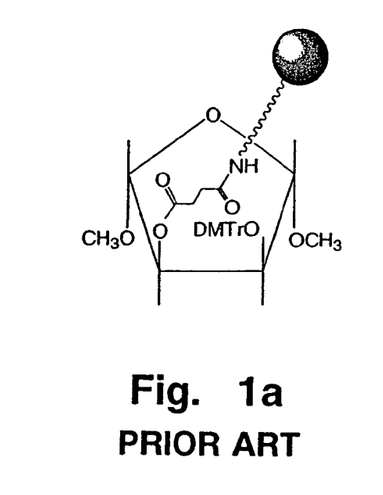
FIGS. 1a to 1d illustrate the chemical structure of various known supports for DNA and RNA synthesis.

Certain known universal supports based on the ribonucleoside elimination model are known as "McLean supports." See S. Scott, P. Hardy, R. C. Sheppard, and M. J. McLean, "A Universal Support for Oligonucleotide Synthesis," *Innovation and Perspectives in Solid Phase Synthesis,* 3rd International Symposium, 1994, pp. 115-124, which document is entirely incorporated herein by reference. McLean supports also are described in U.S. Pat. Nos. 5,681,945 and 5,886,193, which patents are entirely incorporated herein by reference. A McLean support also is illustrated in FIG. 1a. This solid support allows the detritylation, the addition of the first nucleoside monomer, and the remainder of the oligomer preparation to proceed without any changes from standard protocols. Elimination of the terminal phosphodiester group utilizes the same reagents needed for routine deprotection of oligonucleotides, but requires more aggressive and lengthy treatment conditions (e.g., concentrated ammonium hydroxide/80° C./17 hours as compared to the standard oligomer deprotection conditions of ammonium hydroxide/55° C./5-6 hours). While these more aggressive conditions are suitable for the preparation of unmodified oligonucleotides, they are not compatible with base-labile nucleoside analogues. Furthermore, prolonged treatment with basic volatile reagents or the need to employ a desalting step in the case of sodium hydroxide make this solid support unattractive for use in industrial multi-well synthesizers.

The instability of RNA to strongly basic conditions is caused by the proximity of the 2'-OH group to the phosphodiester group. Attack of the 2'-OH on the adjacent phosphorus gives rise to an energetically favorable 5-membered transition state, which can open up again to form a mixture of 2'- and 3'-phosphodiester internucleotide linkages, or can lead to chain scission by elimination of the 3'- or 5'-hydroxyl group. In the case of a McLean universal support of FIG. 1a, cleavage from the support by hydrolysis of a succinate or, better, a hydroquinone-O,O'-diacetate (O) linkage, generates a hydroxyl group adjacent to the terminal phosphodiester linkage. Additional base treatment leads to the elimination of the terminal phosphate group and formation of the desired 3'-OH. Wengel and coworkers described a similar strategy using a neighboring hydroxyl group to facilitate elimination. See C. Scheuer-Larsen, C. Rosenbohm, T. J. D. Jorgensen, and J. Wengel, "Introduction of a Universal Solid Support for Oligonucleotide Synthesis," *Nucleosides & Nucleotides,* 1997, Vol. 16, pp. 67-80, which article is entirely incorporated herein by reference. Lyttle and a group at Biosearch Technologies described a variation of the Wengel procedure. The Lyttle procedure used a linkage to a polymeric support that is not hydrolyzed by base, so that extended base treatment releases the dephosphorylated oligo, while leaving any undesired by-product still attached to the support. See M. H. Lyttle, D. J. Dick, D. Hudson, and R. M. Cook, "A Phosphate Bound Universal Linker for DNA Synthesis," *Nucleosides & Nucleotides,* 1999, Vol. 18, pp. 1809-1824, which article is entirely incorporated herein by reference.

The main impediment to adoption of a universal support has been the aggressively basic conditions required to complete the elimination reaction to release the terminal hydroxyl group. The standard reagents used in oligonucleotide deprotection are ammonium hydroxide and aqueous methylamine, which are popular because they are readily available and completely volatile. Using these reagents to carry out the elimination reaction, however, requires either high temperature, with attendant high pressure, or extended reaction times. The situation can be improved by adding metal ions to the mix (such as Li+, Na+, and Zn2+), to speed up the elimination reaction, presumably by stabilizing the 5-membered transition state. However, the speed and simplicity of evaporation of the deprotection solution to give the crude oligonucleotide without desalting is not possible when these ionic additives are used.

Figure 1B:
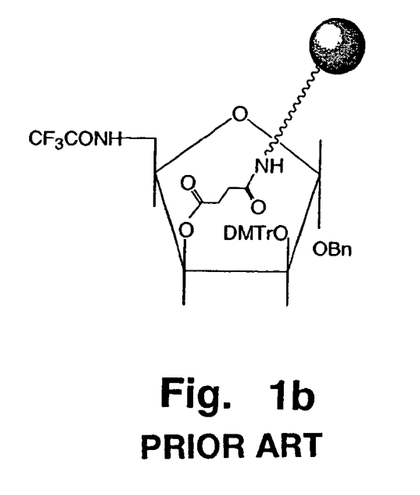
Figure 1C:
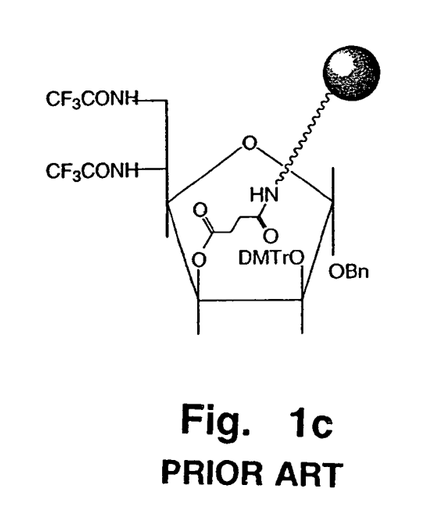
Figure 1D:
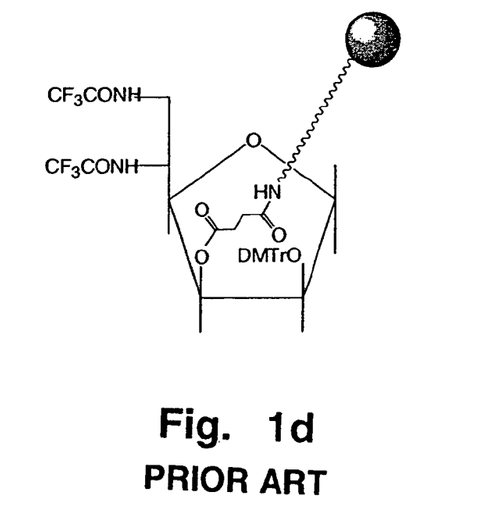

Other known universal supports that use neighboring aminomethyl or diamino-ethyl groups to assist the elimination reaction have been described by Azhayev. See A. V. Azhayev, "A New Universal Solid Support for Oligonucleotide Synthesis," *Tetrahedron,* 1999, Vol. 55, pp. 787-800, which article is entirely incorporated herein by reference. These supports, which are illustrated in FIGS. 1b, 1c, and 1d, are not only compatible with the preparation of all common types of oli- gonucleotides, but they also function well for oligomers with unusual base labile nucleoside units. Using volatile ammonium hydroxide or aqueous methylamine with these supports (e.g., concentrated ammonium hydroxide/80° C./2-8 hours), 3'-terminal dephosphorylation was significantly speeded up, and dephosphorylation could be achieved under neutral conditions using aqueous zinc chloride or water. In these supports, the neighboring aminomethyl- or diaminoethyl-groups assist for the elimination of the terminal phosphodiester to generate termini with 3'-hydroxyl.

While the universal supports of FIGS. 1b-1d offer genuine advantages, especially if the oligonucleotides contain base-labile components, they still are not ideal for mainstream applications. These supports still require relatively long treatment times with basic volatile reagents at elevated temperatures. These features make these supports somewhat unattractive for industrial applications.

Accordingly, there is a need in the art for a universal support suitable for DNA and RNA synthesis that eliminates the drawbacks mentioned above. A desirable universal support would allow fast cleavage and dephosphorylation at relatively low temperatures (e.g., in 20 minutes at room temperature), and under relatively mild reaction conditions (e.g., using a 2M ammonia in methanol cleavage reagent). Moreover, the desired universal support would be compatible for use under ultra-mild, normal, and ultra-fast deprotection conditions. Finally, the desired universal support product will be cost-effective (e.g., comparable in price to regular 2'-deoxynucleoside supports).

SUMMARY OF THE INVENTION

The present invention relates to universal supports for oligonucleotide, DNA, and RNA synthesis, as well as to methods of making and using the supports. A first aspect of the invention relates to a universal support material represented by the following formula:

In this formula, substituent A may be H, an alkyl group, an aryl group, a polymeric base material, or a silica base material; substituent B may be an acyl group, an aroyl group, a polymeric base material, or a silica base material; and substituent C may be a dimethoxytrityl group or another protecting group removable under acidic or neutral conditions. For the support material according to this formula, one of substituent A or B constitutes a polymeric base material or a silica base material.

In one embodiment of the invention, substituent A constitutes the polymeric or silica base material. As one example, the silica base material of substituent A may be a long chain alkylamino controlled pore glass base material. As an even more specific example, substituent A may include the following substituent:

wherein lcaaCPG and its accompanying substituent groups represent a long chain alkylamino controlled pore glass base material. As illustrative examples, in this embodiment of the invention (where substituent A is the base material), substituent B may be an acyl group (e.g., a formyl group or an acetyl group) or an aroyl group (e.g., a phenoxyacetyl group). Also, optionally, the acyl or aroyl groups may be substituted with halogen atoms (e.g., chloroacetyl, dichloroacetyl, 4-chlorophenoxyacetyl, and 2,4-dichlorophenoxyacetyl). Other suitable substituent groups can be used as substituent B without departing from the invention.

In another embodiment of the invention, substituent B may constitute the polymeric or silica base material. As one example, the silica base material of substituent B may be a long chain alkylamino controlled pore glass base material. As an even more specific example, substituent B may include the following substituent group:

wherein lcaaCPG and its accompanying substituent groups represent the long chain alkylamino controlled pore glass base material. In this embodiment, substituent A may be various suitable substituent groups. Examples of these suitable substituent groups include: hydrogen, an alkyl group and a phenyl group, and optionally these groups can be substituted, e.g., with halogen atoms. More specific examples of suitable substituent groups useful as substituent A include: a —CF$_3$ group, a methyl group, an ethyl group, a propyl group, a butyl group, and a t-butyl group.

A second aspect of the present invention relates to articles of manufacture represented by the following formula:

wherein substituent A may be H, an alkyl group, an aryl group, a polymeric base material, or a silica base material; substituent B may be an acyl group, an aroyl group, a polymeric base material, or a silica base material; and substituent

C may be a dimethoxytrityl group, a nucleotide-containing group, or a protecting group removable under acidic or neutral conditions. Again, in this aspect of the invention, one of substituents A or B constitutes a polymeric base material or a silica base material. In this aspect of the invention, substituents A and B may constitute the various groups described above with respect to the first aspect of the invention.

In these articles of manufacture according to the invention, substituent C may be a nucleotide-containing group. In other words, this aspect of the invention also relates to the solid supports according to the invention with one or more nucleotides supported thereon. For example, the nucleotide-containing group supported on the universal support may include at least one nucleotide selected from the group consisting of: thymidine, 2'-deoxyadenosine, 2'-deoxycytindine, and 2'-deoxyguanosine. The nucleotide-containing group may be attached to the support via a phosphotriester group (at substituent C).

Various specific support materials according to the invention include the following:

In these illustrated formulae, "DMTr" represents a dimethoxytrityl group, and "lcaaCPG" and its accompanying substituent groups represent a long chain alkylamino controlled pore glass base material. This invention also relates to the resulting articles of manufacture produced when one or more nucleotides are supported on the above support materials, e.g., via a phosphotriester linkage at the DMTr group.

Another aspect of this invention relates to an article of manufacture represented by the following formula:

wherein X represents =O, S, or NH; Y represents O or NH; substituent A represents H, an alkyl group, an aryl group, a polymeric base material, a silica base material, a substituent including an activated ester capable of coupling to an amino support, or a substituent terminating in a phosphoramidite group capable of coupling to a support or an oligonucleotide; substituent B represents a first protecting group; and substituent C represents a second protecting group that is different from the first protecting group. In this aspect of the invention, one of the first protecting group or the second protecting group is a substituent group capable of being removed under neutral conditions (e.g., a base-labile protecting group, such as dichloroacetyl or other acyl or aroyl groups), and the other of the first protecting group or the second protecting group is a substituent group capable of being removed under acidic or specific neutral conditions. For example, in one embodiment of this aspect of the invention, substituent B may be a base-labile group, such as an acyl or an aroyl group, and substituent C may be a dimethoxytrityl group. In another embodiment of this aspect of the invention, substituent C may be a base-labile group, such as an acyl group or an aroyl group, and substituent B may be a dimethoxytrityl group.

Another aspect of this invention relates to use of the support products. In one embodiment, this invention relates to a method for releasing a product oligonucleotide from a support by treating a supported oligonucleotide with a nonaqueous base (which may be an anhydrous base). In this embodiment of the invention, the supported oligonucleotide is represented by the following formula:

wherein substituent A includes H, an alkyl group, an aryl group, or a polymeric or silica support material, substituent B is an acyl group, an aroyl group, or a polymeric or silica support, and substituent C is an oligonucleotide-containing group, with the proviso that one of substituents A or B constitutes a polymeric or silica support material. This nonaqueous base treatment acts to cleave substituent A or B (whichever is not the polymeric or silica support) from the supported oligonucleotide. Thereafter, the supported oligonucleotide is further treated to separate the product oligonucleotide (included as part of substituent C) from the support (included as part of substituent A or B). The nonaqueous base used in the initial treatment step may include ammonia gas or ammonia, such as ammonia in an alcohol solution (e.g., in methanol).

Various support materials described above may be used in performing this method. For example, substituent A may include a long chain alkylamino controlled pore glass base material. In this instance, as additional examples, substituent B may be a chloroacetyl group, a dichloroacetyl group, a 4-chlorophenoxyacetyl group, a 2,4-dichlorophenoxyacetyl group, or any of the other substituent groups mentioned above.

Specific examples of the supported oligonucleotide in this embodiment of the invention include the following:

and wherein lcaaCPG and its accompanying substituent groups represent a long chain alkylamino controlled pore glass base material. The oligonucleotide-containing group may be attached via a phosphotriester group.

BRIEF DESCRIPTION OF THE DRAWINGS

Various aspects of this invention are described in conjunction with the attached drawings, wherein.

DETAILED DESCRIPTION OF THE INVENTION

As described above, this invention relates to universal supports used in oligomer, RNA, and DNA synthesis. The universal supports according to the invention allow for faster elimination of the 3'-terminal phosphodiester group under relatively mild elimination conditions (e.g., using methanolic ammonia solutions at room temperature).

Any solid support material suitable for use in oligonucleotide synthesis can be used with this invention. For example, the solid supports described in the patent and literature identified in the "Background" section of this document can be used in conjunction with the invention. The solid supports can be beads, particles, sheets, dipsticks, rods, membranes, filters, fibers (e.g., optical or glass), or in any other suitable form. The material composition of the solid support materials may be any suitable materials, such as polymeric or silica based support materials. Specific examples, include plastic, nylon, glass, silica, metal, metal alloy, polyacrylamide, polyacrylate, polystyrene, cross-linked dextran, and combinations thereof. The term "silica base material" or "silica support material," as used in the present specification and claims, includes glass materials, unless it is specifically indicated that glass materials are not included.

The following definitions apply to the specification and claims, unless another definition is clearly provided.

The term "alkyl," as used herein, refers to substituted or unsubstituted, straight or branched chain groups, preferably having one to twelve, more preferably having one to six, and most preferably having from one to four carbon atoms. Illustrative examples of alkyl groups include, but are not limited to: methyl, trifluoromethyl, ethyl, propyl, isopropyl, butyl, isobutyl, t-butyl, pentyl, hexyl, and the like.

The term "aryl," as used herein, refers to an aromatic, monovalent monocyclic, bicyclic, or tricyclic radical containing 6, 10, 14, or 18 carbon ring atoms, which may be unsubstituted or substituted, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to: phenyl, naphthyl, anthryl, phenanthryl, fluoren-2-yl, indan-5-yl, and the like.

Examples of possible substituents for alkyl and aryl groups include: mercapto, thioether, nitro ($NO_2$), amino, aryloxyl, halogen, hydroxyl, alkoxyl, and acyl, as well as aryl, cycloalkyl and saturated and partially saturated heterocycles.

The term "halogen" represents chlorine, fluorine, bromine, or iodine. The term "halo" represents chloro, fluoro, bromo or iodo.

The term "acyl," as used herein, represents substituents of the general formula —C(=O)R, wherein R is hydrogen or an alkyl group. Illustrative examples of acyl groups include formyl, acetyl, chloroacetyl, dichloroacetyl, and propionyl.

The term "aroyl," as used herein, represents an acyl group wherein the R substituent includes an aryl group. Illustrative examples of aroyl groups include phenoxyacetyl groups, halophenoxyacetyl groups (e.g., 4-chlorophenoxyacetyl), dihalophenoxyacetyl (e.g., 2,4-dichlorophenoxyacetyl), and the like.

The term "oligonucleotide" as used in this document has its conventional meaning. The patent and other literature identified in the "Background" section of this document illustrate the meaning of this term. One suitable definition, although not necessarily exclusive or exhaustive, is as follows: the term "oligonucleotide" is generic to polydeoxynucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones, providing that the polymers contain nucleobases in a configuration which allows for base pairing and base stacking, such as is found in DNA and RNA. It will be appreciated that, as used herein, the terms "nucleoside" and "nucleotide" will include those moieties which contain not only the known purine and pyrimidine bases, but also modified purine and pyrimidine bases and other heterocyclic bases which have been modified (these moieties are sometimes referred to collectively as "purine and pyrimidine bases and analogs thereof"). Such modifications include methylated purines or pyrimidines, acylated purines or pyrimidines, and the like.

A wide variety of protecting groups can be employed in the supports of the invention, and examples of suitable protecting groups are described in the patents and other literature identified above. In general, protecting groups render chemical functionality inert to specific reaction conditions, and can be appended to and removed from such functionality in a molecule. Representative protecting groups are disclosed by Beaucage, S. L.; Uyer, R. P., "Advances in the Synthesis of oligonucleotides by the Phosphoramidite Approach," *Tetrahedron*, 1992, 48, 2223-2311, which article is entirely incorporated by reference. Illustrative protecting groups that can be removed under acidic or neutral conditions include trityl (Tr), dimethoxytrityl (DMTr), monomethoxytrityl, 9-phenylxanthen-9-yl (Pixyl), 9-(p-methoxyphenyl)xanthen-9-yl (Mox), and 4,4',4"-tris-tert-butyltrityl (TTTr). Illustrative protecting groups that can be removed under neutral conditions are base-labile protecting groups, such as the acyl or aroyl groups identified above.

All inventive compounds that contain at least one chiral center may exist as single stereoisomers, racemates and/or mixtures of enantiomers and/or diastereomers. All such single stereoisomers, racemates and mixtures thereof are intended to be within the scope of the present invention.

Figure 2:
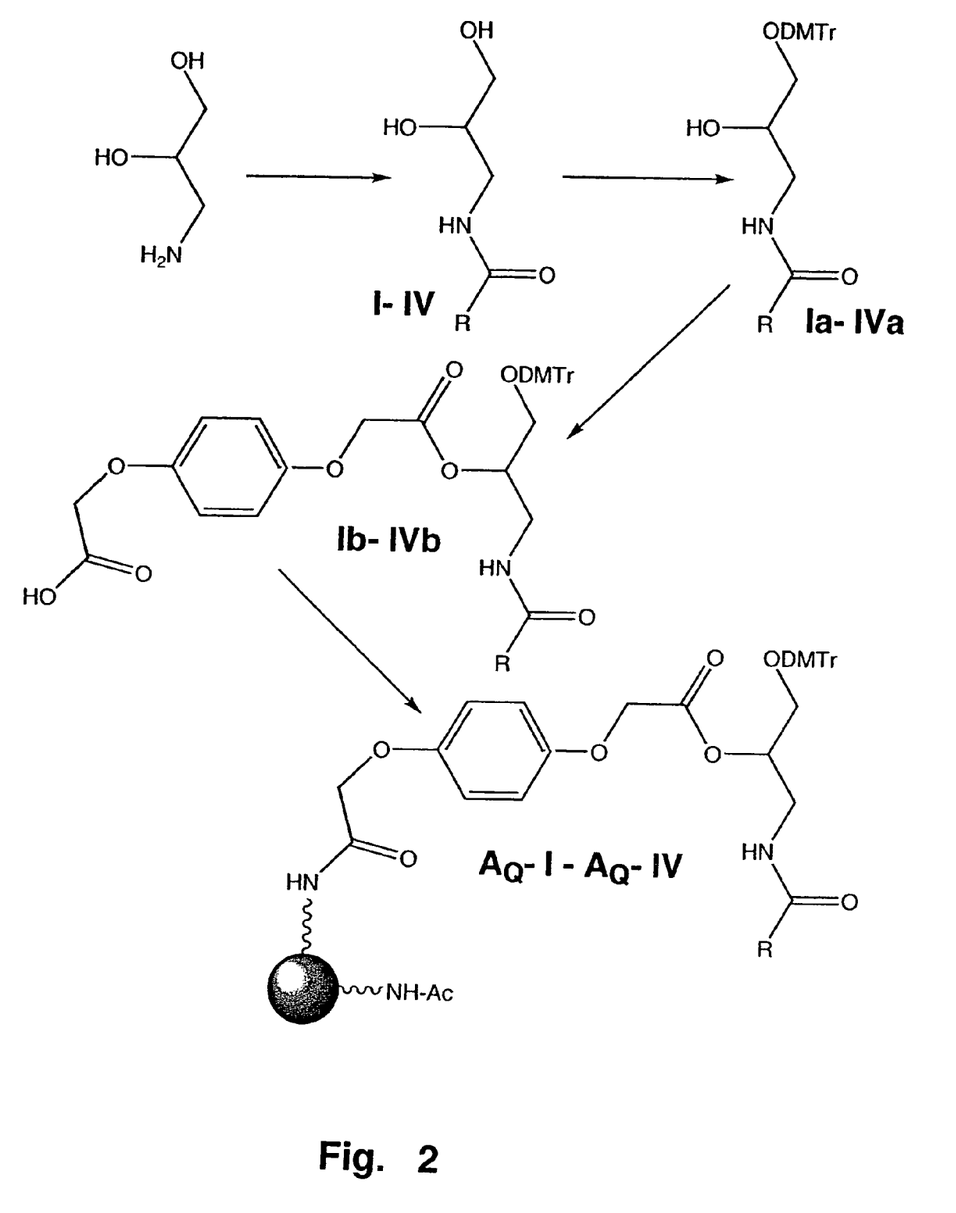
FIG. 2 illustrates a reaction scheme for producing supports $A_Q$-I, $A_Q$-II, $A_Q$-III, and $A_Q$-IV according to the invention in the manner described in the examples.

Specific $A_Q$ solid supports according to the invention are illustrated in FIG. 2 and described in more detail below as supports $A_Q$-I-$A_Q$-IV. In producing these supports, a (±)-3-acylamido-1-(4,4'-dimethoxytriphenylmethyl)-2-propanediol is attached to an lcaa-CPG ("long chain alkylamino controlled pore glass") substrate via a hydroquinone-O,O'-diacetyl linker. In general, one suitable synthesis procedure for these supports according to the invention is as follows (and as illustrated in FIG. 2). First, a starting (±)-3-amino-1, 2-propanediol material was acylated to give 3-acylamido derivatives I-IV. These intermediates were then converted into dimethoxytrityl derivatives Ia-IVa. The 2-hydroxy groups of intermediates Ia-IVa were acylated with hydroquinone-O,O'-diacetic acid and N,N'-di-isopropylcarbodiimide to give compounds Ib-IVb. Finally, derivatives Ib-IVb were linked to an lcaaCPG, employing N,N'-di-isopropylcarbodiimide/N-hydroxybenzotriazole condensation. The resulting solid supports $A_Q$-I-$A_Q$-IV contained 40-100 mmols of DMTr-groups per gram of CPG.

While preparation of supports $A_f$ and $A_p$ according to the invention is described in detail below (see also FIG. 3), a brief general description follows. Initially, an lcaaCPG was succinylated and capped to give succinylamodo-CPG (Compound VI). Separately, (±)-3-trifluoroacetamido-1-(4,4'-dimethoxytriphenylmethyl)-2-propanediol (Compound Ia from FIG. 2) was converted to the corresponding amine, Compound V, which, in turn, was attached to Compound VI in the presence of N,N'-di-isopropylcarbodiimide and N-hydroxybenzotriazole to give solid phase Compound VII. Finally, the free hydroxyl group of Compound VII was either formylated to give solid support $A_f$ or phenoxyacetylated to give support $A_p$. These resulting solid supports $A_f$ and $A_p$ each contained about 100 μmols of DMTr-groups per gram of CPG.

I. Experimental Section

Production of universal supports according to the invention will now be described in conjunction with various specific examples. These examples should be construed as illustrating the invention, not as limiting it.

A. General Background Information Relating to the Examples

In the experiments described below, the (±)-3-amino-1,2-propanediol starting material may be obtained from Fluka. Acetic anhydride, benzoyl chloride, pivaloil chloride, 2,6-lutidine, succinic anhydride, trifluoroacetic acid, and all solvents are all known and commercially available, e.g., from Aldrich. 4,4'-Dimethoxytrityl chloride may be obtained from ChemGenes, and the long chain alkylamino controlled pore glass ("lcaaCPG") may be obtained from various sources, such as Sigma and Glen Research. The hydroquinone-O,O' diacetic acid used in the examples may be obtained from Lancaster. The reagents (solvents, activators, etc.) for oligonucleotide synthesis may be obtained from Glen Research.

Unless otherwise noted, the following equipment and test conditions were used in the experiments described below. Column flash chromatography was performed on Silica gel 60 (available from Merck). NMR spectra were recorded on a Brucker 500 spectrometer with tetramethylsilane as an internal standard (the following abbreviations are used in describing the NMR spectra: s=singlet; d=doublet; dd=doublet of doublet; m=multiplet; br.s=broad signal). All compounds bearing free hydroxy- and amino-groups were co-evaporated with $CD_3OD$ before measurements were taken.

Oligonucleotides were analyzed by ion exchange HPLC (column: Dionex DNAPac PA-100, 4×250 mm, buffer A: 0.1 M NaAc in 20% MeCN, pH8, buffer B: 0.1 M NaAc and 0.4 M $NaClO_4$ in 20% MeCN, pH8; flow rate 1 ml min$^{-1}$; a linear gradient from 0 to 15% B in 20 minutes for oligo-$T_6$ and modified oligo-$T_6$ oligonucleotides and from 5 to 45% B in 30 minutes for longer oligomers). Phosphorothioate oligonucleotides were analyzed by ion exchange HPLC (column: Poly LP PolyWax 4.6×100 mm, 5 μm, 300 Å, buffer A: 0.05 M $KH_2PO_4$ in 50% formamide, pH 6.7, buffer B: 0.05 M $KH_2PO_4$ and 1.5 M NaBr in 50% formamide, pH 6.7; flow rate 1 ml min$^{-1}$; a linear gradient from 5 to 50% B in 30 min).

In the oligodeoxyribonucleotide synthesis described below, the protected oligonucleotides were assembled on an Applied Biosystems 392 DNA Synthesizer using phosphoramidite chemistry and recommended DMTr-off protocols for 40 nmol, 0.2 μmol, and 1 μmol scale.

Figure 3:
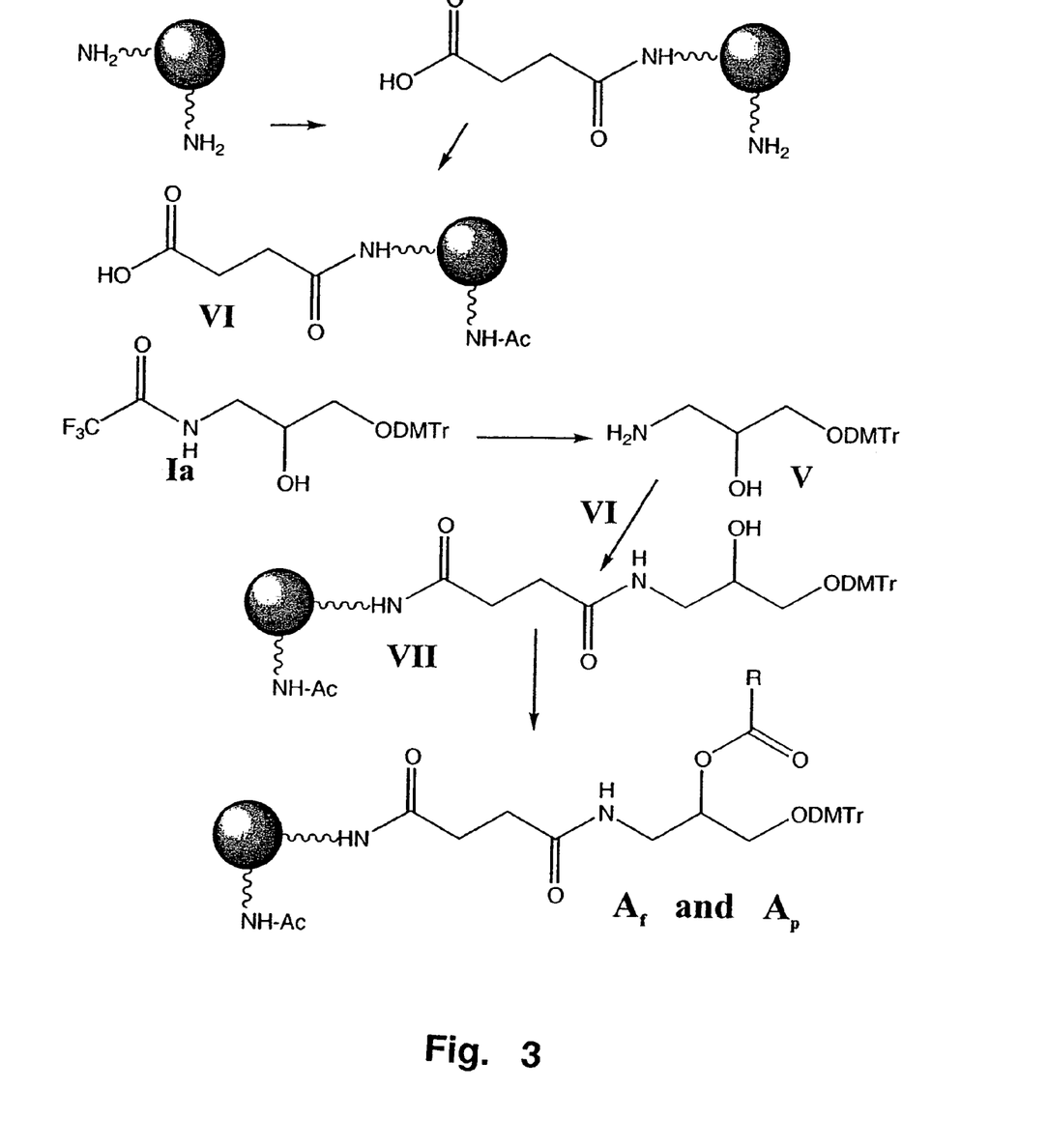
FIG. 3 illustrates a reaction scheme for producing supports $A_f$ and $A_p$ according to the invention in the manner described in the examples.

The figures also illustrate reaction schemes from the following examples in more detail. Supports $A_Q$-I, $A_Q$-II, $A_Q$-III, and $A_Q$-IV are prepared according to the reaction scheme illustrated in FIG. 2. For Compounds I, Ia, Ib, and $A_Q$-I, substituent R in FIG. 2 is a trifluoromethyl group (—$CF_3$). For Compounds II, IIa, IIb, and $A_Q$-II, substituent R in FIG. 2 is a methyl group (—$CH_3$). For Compounds III, IIIa, IIIb, and $A_Q$-III, substituent R in FIG. 2 is a phenyl group (—$C_6H_5$). For Compounds IV, IVa, IVb, and $A_Q$-IV, substituent R in FIG. 2 is a t-butyl group (—$C(CH_3)_3$). Supports $A_f$ and $A_p$ are prepared according to the reaction scheme illustrated in FIG. 3. For Compound $A_f$, substituent R in FIG. 3 is a hydrogen atom. For Compound $A_p$, substituent R in FIG. 3 is a —$CH_2$—O—$C_6H_5$ group.

B. Preparation of Support $A_Q$-I

1. Preparation of (±)-3-Trifluoroacetamido-1,2-propanediol (Compound I)

Compound I as illustrated in FIG. 2 was prepared as follows. (±)-3-amino-1,2-propanediol (2.73 g, 30 mmol) was dissolved in methyl trifluoroacetate (30 mL, 300 mmol) and left overnight at 20° C. The reaction mixture was evaporated and dried by co-evaporating with toluene (3×100 ml) to give 5.44 g (97%) of Compound I as a colorless oil: $^1$H NMR ($CDCl_3$): δ=6.82, br.s, 1H, NH; 3.92, m, $J^3$=4.1, H-2; 3.73, m, 1H, $J^2$=11.0, H-1$_a$; 3.62 m, 1H, $J^2$=14.1, H-3$_a$; 3.57, m, 1H, H-1$_b$; 3.42, m, 1H, H-3$_b$. Found: C, 31.89; H, 4.47; N, 7.40. Calculated for $C_5H_8F_3NO_3$: C, 32.09; H, 4.31; N, 7.49%.

2. Preparation of (±)-3-Trifluoroacetamido-1 (4,4'-dimethoxytriphenylmethyl)-2-propanediol (Compound Ia)

Compound Ia as illustrated in FIG. 2 was prepared as follows. 4,4'-Dimethoxytrityl chloride (1.7 g, 5 mmol) was added to a stirred solution of 5 mmol of Compound I in dry pyridine (20 ml). The mixture was agitated overnight at 20° C., and then the reaction was stopped by addition of 2 ml of methanol. Solvents were removed by evaporation, the residue was dissolved in 50 ml of ethyl acetate and then washed with saturated sodium hydrocarbonate solution (3×30 ml) and water (2×30 ml). The organic solution was dried over $Na_2SO_4$ and evaporated to dryness. (±)-3-Trifluoroacetamido-1(4,4'-dimethoxytriphenylmethyl)-2-propanediol (Compound Ia) was isolated by flash chromatography (step gradient from 0 to 2% of methanol in dichloromethane in the presence of 0.1% of pyridine) as a pale yellow oil.

The yield of Compound Ia was 1.98 g, 81%: $^1$H NMR ($CDCl_3$): δ=8.52, br.s, 1H, NH; 7.43-6.81, m, 13H, arom.; 3.91, m, H-2; 3.78, s, 6H, $OCH_3$; 3.57, dd, 1H, $J^3$=3.3, $J^2$=14.6, H-3$_a$; 3.30 dd, 1H, $J^3$=7.6, H-3$_b$; 3.17, d, 2H, $J^3$=7.6, H-1$_{a,b}$. Found: C, 64.01; H, 6.03; N, 2.52. Calculated for $C_{27}H_{30}F_3NO_5$: C, 64.15; H, 6.03; N, 2.77%.

3. Coupling of hydroquinone-O,O'-diacetic acid to Compound Ia to provide Compound Ib Compound Ib illustrated in FIG. 2 was prepared as follows. Hydroquinone-O,O'-diacetic acid (0.452 g, 2 mmol) was dissolved in 5 ml of dry pyridine-dimethylformamide (4:1). N,N'-di-isopropylcarbodiimide (0.16 ml, 1 mmol) was added, and the mixture was left for 1 hour at 20° C. The resulting solution was added to a solution of Compound Ia (1 mmol) and 4-N,N-dimethylaminopyridine (10 mg) in dry pyridine (3 ml). The reaction mixture was left overnight at 20° C. Water (1 ml) was then added, and the resulting mixture was evaporated to dryness. Compound Ib was isolated by flash chromatography (step gradient from 0 to 5% of methanol in dichloromethane in the presence of 0.1% of pyridine) as a pale yellow oil.

The yield of Compound Ib was 0.45 g (65%); $^1$H NMR ($CDCl_3/CD_3OD$, 4:1): δ=7.45-6.82, m, 17H, arom.; 5.17, br.s, 1H NH; 4.58, br.s, 4H, $OCOCH_2$; 3.79, s, 6H, $OCH_3$; 3.77, m, 1H, H-2; 3.48, m, 2H, H-3$_{a,b}$; 3.26, m, 2H, H-1$_{a,b}$. Found: C, 62.21; H, 4.99; N, 1.89. Calculated for $C_{36}H_{34}F_3NO_{10}$: C, 61.98; H, 4.91; N, 2.01%.

4. Preparation of Support $A_Q$-I

A mixture of lcaa-CPG (0.3 g), hydroxybenzotriazole (HOBT) (30 mg, 0.2 mmol), N,N'-di-isopropylcarbodiimide (35 μl, 0.2 mmol), and the conjugate of Compound Ia and hydroquinone-O,O'-diacetic acid (i.e., Compound IIb prepared above, 0.15 mmol) in pyridine (5 ml) was agitated overnight at 20° C. The solids were filtered off, washed with pyridine (5 ml), tetrahydrofuran (5 ml), diethyl ether (10 ml), and dried. The resulting support was suspended in a mixture of 1-methylimidazole:tetrahydrofuran (4:21; 5 ml) and acetic anhydride-2,6-lutidine-tetrahydrofuran (1:1:8; 5 ml), agitated for 45 minutes at 20° C., filtered off, washed with tetrahydrofuran (5 ml), acetonitrile (10 ml), diethyl ether (10 ml), and dried. The resulting support $A_Q$-I contained 100 μmol of DMTr-groups per gram of CPG.

C. Preparation of Support $A_Q$-II

1. Preparation of (O)-3-acetamido-1,2-propanediol (Compound II)

Compound II as illustrated in FIG. 2 was prepared as follows. (±)-3-amino-1,2-propanediol (0.91 g, 10 mmol) was dissolved in 20 mL of dry pyridine, and acetic anhydride (4.7 ml, 50 mmol) was added. The mixture was left overnight at 20° C. and evaporated. The oily residue was treated with 25% aqueous ammonia (30 ml) for 1 hour at 20° C. After evaporation and drying by co-evaporation with toluene (3×50 mL), compound II was used for 4,4'-dimethoxytritylation without further purification.

2. Preparation of (±)-3-acetamido-1(4,4'-dimethoxytriphenylmethyl)-2-propanediol (Compound IIa)

Compound Ia as illustrated in FIG. 2 was prepared as follows. 4,4'-Dimethoxytrityl chloride (1.7 g, 5 mmol) was added to a stirred solution of 5 mmol of Compound II in dry pyridine (20 ml). The mixture was agitated overnight at 20° C., and then the reaction was stopped by addition of 2 ml of methanol. Solvents were removed by evaporation, the residue was dissolved in 50 ml of ethyl acetate and then washed with saturated sodium hydrocarbonate solution (3×30 ml) and water (2×30 ml). The organic solution was dried over $Na_2SO_4$ and evaporated to dryness. (±)-3-acetamido-1(4,4'-dimethoxytriphenylmethyl)-2-propanediol (Compound IIa) was isolated by flash chromatography (step gradient from 0 to 5% of methanol in dichloromethane in the presence of 0.1% of pyridine) as a pale yellow oil.

The yield of Compound IIa was 1.7 g, 78%: $^1$H NMR ($CDCl_3$): δ=7.40-6.80, m, 13H, arom.; 6.12, br.s, 1H, NH; 3.88, m, H-2; 3.79, s, 6H, $OCH_3$; 3.52, m, 1H, $J^3$=3.7, $J^3$=13.3, H-$3_a$; 3.38 m, 1H, H-$3_b$; 3.28, m, 1H, $J^3$=5.7, H-$1_a$; 3.19, m, 1H, H-$1_b$; 2.01, s, 3H, $CH_3CONH$. Found: C, 71.51; H, 6.92; N, 3.01. Calculated for $C_{26}H_{29}NO_5$: C, 71.70; H, 6.71; N, 3.22%.

3. Coupling of hydroquinone-O,O'-diacetic acid to Compound Ia to provide Compound IIb Compound IIb illustrated in FIG. 2 was prepared as follows. Hydroquinone-O,O'-diacetic acid (0.452 g, 2 mmol) was dissolved in 5 ml of dry pyridine:dimethylformamide (4:1). N,N'-di-isopropylcarbodiimide (0.16 ml, 1 mmol) was added, and the mixture was left for 1 hour at 20° C. The resulting solution was added to a solution of Compound IIa (1 mmol) and 4-N,N-dimethylaminopyridine (10 mg) in dry pyridine (3 ml), and the reaction mixture was left overnight at 20° C. Water (1 ml) was then added, and the resulting mixture was evaporated to dryness. Crude Compound IIb was dried in high vacuum to give 0.37 g of a pale yellow oil, which was used for $A_Q$-II support preparation without any further purification.

4. Preparation of Support $A_Q$-II

A mixture of lcaa-CPG (0.3 g), hydroxybenzotriazole (HOBT) (30 mg, 0.2 mmol), N,N'-di-isopropylcarbodiimide (35 µl, 0.2 mmol), and the conjugate of Compound IIa and hydroquinone-O,O'-diacetic acid (i.e., Compound IIb prepared above, 0.15 mmol) in pyridine (5 ml) was agitated overnight at 20° C. The solids were filtered off, washed with pyridine (5 ml), tetrahydrofuran (5 ml), diethyl ether (10 ml), and dried. The resulting support was suspended in a mixture of 1-methylimidazole:tetrahydrofuran (4:21; 5 ml) and acetic anhydride-2,6-lutidine-tetrahydrofuran (1:1:8; 5 ml), agitated for 45 minutes at 20° C., filtered off, washed with tetrahydrofuran (5 ml), acetonitrile (10 ml), diethyl ether (10 ml), and dried. The resulting support $A_Q$-II contained 50 µmol of DMTr-groups per gram of CPG.

D. Preparation of Support $A_Q$-III

1. Preparation of (±)-3-benzoylamido-1,2-propanediol (Compound III)

Compound III as illustrated in FIG. 2 was prepared as follows. Benzoyl chloride (0.7 ml, 6 mmol) in 1,4-dioxane (5 ml) was added dropwise to a cold (0° C.) stirred solution of (±)-3-amino-1,2-propanediol (0.55 g, 6 mmol) in 1,4-dioxane: water (5:1; 20 ml). The reaction mixture was allowed to warm up to 20° C. within 2 hours, and the solvents were then removed in vacuum. Compound III was isolated by flash chromatography (isocratic, 7% methanol in dichloromethane) as a colorless oil (0.83 g, 71%): $^1$H NMR ($CDCl_3$): δ=10.05, br.s, 1H, NH; 8.06-7.13, m, 5H, arom.; 3.93, m, $J^3$=4.1, $J^3$=4.7, H-2; 3.60 m, 4H, H-$1_{a,b}$ and H-$3_{a,b}$. Found: C,61.39; H, 6.83; N, 7.02. Calculated for $C_{10}H_{13}NO_3$: C, 61.53; H, 6.71; N, 7.18%.

2. Preparation of (±)-3-benzoylamido-1-(4,4'-dimethoxytriphenylmethyl)-2-propanediol (Compound IIIa)

Compound IIIa as illustrated in FIG. 2 was prepared as follows. 4,4'-Dimethoxytrityl chloride (1.7 g, 5 mmol) was added to a stirred solution of 5 mmol of Compound III in dry pyridine (20 ml). The mixture was agitated overnight at 20° C., and then the reaction was stopped by addition of 2 ml of methanol. Solvents were removed by evaporation, the residue was dissolved in 50 ml of ethyl acetate and then washed with saturated sodium hydrocarbonate solution (3×30 ml) and water (2×30 ml). The organic solution was dried over $Na_2SO_4$ and evaporated to dryness. (±)-3-benzoylamido-1-(4,4'-dimethoxytriphenylmethyl)-2-propanediol (Compound IIIa) was isolated by flash chromatography (step gradient from 0 to 2% of methanol in dichloromethane in the presence of 0.1% of pyridine) as a pale yellow oil.

The yield of Compound IIIa was 2.1 g, 85%: $^1$H NMR ($CDCl_3$): δ=7.64-6.80, m, 18H, arom.; 6.48, br.s, 1H, NH; 3.86, m, 3.77, s, 6H, $OCH_3$; H-2; 3.60, m, 3H, H-$1_a$ and H-$3_{a,b}$; 3.46, m, 1H, $J^3$=5.3, $J^2$=11.8. Found: C, 75.06; H, 6.30; N, 2.69. Calculated for $C_{31}H_{31}NO_5$: C, 74.83; H, 6.28; N, 2.81%.

3. Coupling of hydroquinone-O,O'-diacetic acid to Compound IIIa to provide Compound IIIb Compound IIIb illustrated in FIG. 2 was prepared as follows. Hydroquinone-O,O'-diacetic acid (0.452 g, 2 mmol) was dissolved in 5 ml of dry pyridine-dimethylformamide (4:1). N,N'-di-isopropylcarbodiimide (0.16 ml, 1 mmol) was added, and the mixture was left for 1 hour at 20° C. The resulting solution was added to a solution of Compound IIIa (1 mmol) and 4-N,N-dimethylaminopyridine (10 mg) in dry pyridine (3 ml), and the reaction mixture was left overnight at 20° C. Water (1 ml) was then added, and the resulting mixture was evaporated to dryness. Compound IIIb was isolated by flash chromatography (step gradient from 0 to 5% of methanol in dichloromethane in the presence of 0.1% of pyridine) as a pale yellow oil.

The yield of Compound IIIb was 0.48 g (69%); $^1$H NMR ($CDCl_3/CD_3OD$, 4:1): δ 7.88-6.81, m, 22H, arom.; 5.17, 4.56, br.s, 4H, $OCOCH_2$; 3.97, m, 1H, H-2; 3.79, s, 6H, $OCH_3$; 3.68, m, 2H, H-$3_{a,b}$; 3.37, m, 2H, H-$1_{a,b}$. Found: C, 70.93; H, 5.41; N, 1.82. Calculated for $C_{41}H_{39}NO_{10}$: C, 74.83; H, 6.28; N, 2.81%.

4. Preparation of Support $A_Q$-III

A mixture of lcaa-CPG (0.3 g), hydroxybenzotriazole (HOBT) (30 mg, 0.2 mmol), N,N'-di-isopropylcarbodiimide (35 µl, 0.2 mmol), and the conjugate of Compound IIIa and hydroquinone-O,O'-diacetic acid (i.e., Compound IIIb prepared above, 0.15 mmol) in pyridine (5 ml) was agitated overnight at 20° C. The solids were filtered off, washed with pyridine (5 ml), tetrahydrofuran (5 ml), diethyl ether (10 ml), and dried. The resulting support was suspended in a mixture of 1-methylimidazole:tetrahydrofuran (4:21; 5 ml) and acetic anhydride-2,6-lutidine-tetrahydrofuran (1:1:8; 5 ml), agitated for 45 minutes at 20° C., filtered off, washed with tetrahydrofuran (5 ml), acetonitrile (10 ml), diethyl ether (10 ml), and dried. The resulting support $A_Q$-III contained 40 µmol of DMTr-groups per gram of CPG.

E. Preparation of Support $A_Q$-IV

1. Preparation of (±)-3-pivaloylamido-1,2-propanediol (Compound IV)

Compound IV as illustrated in FIG. 2 was prepared as follows. Pivaloyl chloride (0.74 ml, 6 mmol) in 5 ml of 1,4-dioxane was added dropwise to a cold stirred solution (0° C.) of (±)-3-amino-1,2-propanediol (0.55 g, 6 mmol) in 1,4-dioxane water (5:1; 20 ml). The reaction mixture was allowed to warm up to 20° C. within 2 hours. The solvents were removed in vacuum, and Compound IV was isolated by flash chromatography (isocratic, 7% of methanol in dichloromethane) as a colorless oil (0.8 g, yield 77%): $^1$H NMR ($CDCl_3$): δ=6.96, br.s, 1H, NH; 3.78, m, 1H, H-2; 3.67, m, 1H, $J^3$=4.2, $J^2$=10.7, H-1$_a$; 3.47 m, 1H, H-3$_a$; 3.40, m, 1H, H-1$_b$; 3.40, m, 1H, J$^3$=5.0, J$^2$=11.7, H-3$_b$; 1.20, s, 9H, CH$_3$. Found: C, 54.71; H, 9.91; N, 7.83. Calculated for C$_8$H$_{17}$NO$_3$: C, 54.84; H, 9.78; N, 7.99%.

2. Preparation of (±)-3-pivaloylamido-1-(4,4'-dimethoxytriphenylmethyl)-2-propanediol (Compound IVa)

Compound IVa as illustrated in FIG. 2 was prepared as follows. 4,4'-Dimethoxytrityl chloride (1.7 g, 5 mmol) was added to a stirred solution of 5 mmol of Compound IV in dry pyridine (20 ml). The mixture was agitated overnight at 20° C., and then the reaction was stopped by addition of 2 ml of methanol. Solvents were removed by evaporation, the residue was dissolved in 50 ml of ethyl acetate and then washed with saturated sodium hydrocarbonate solution (3×30 ml) and water (2×30 ml). The organic solution was dried over Na$_2$SO$_4$ and evaporated to dryness. (±)-3-pivaloylamido-1-(4,4'-dimethoxytriphenylmethyl)-2-propanediol (Compound IVa) was isolated by flash chromatography (step gradient from 0 to 2% of methanol in dichloromethane in the presence of 0.1% of pyridine) as a pale yellow oil.

The yield of Compound IVa was 1.76 g, 74%: $^1$H NMR (CDCl$_3$): δ=7.41-6.81, m, 13H, arom.; 5.94, br.s, 1H, NH; 3.93, m, 1H, H-2; 3.77, s, 6H, OCH$_3$; 3.51, m, 1H, J$^3$=4.4, J$^2$=12.1, H-3$_a$; 3.42 m, 1H, H-3$_b$; 3.28, m, 1H, J$^3$=5.5, J$^2$=11.3, H-1$_a$; 3.11, m, 1H, H-1$_b$; 1.11, s, 9H, CH$_3$. Found: C, 73.12; H, 7.48; N, 2.79. Calculated for C$_{29}$H$_{35}$NO$_5$: C, 72.93; H, 7.48; N, 2.93%.

3. Coupling of hydroquinone-O,O'-diacetic acid to Compound IVa to provide Compound IVb Compound IVb illustrated in FIG. 2 was prepared as follows. Hydroquinone-O,O'-diacetic acid (0.452 g, 2 mmol) was dissolved in 5 ml of dry pyridine-dimethylformamide (4:1). N,N'-di-isopropylcarbodiimide (0.16 ml, 1 mmol) was added, and the mixture was left for 1 hour at 20° C. The resulting solution was added to a solution of Compound IVa (1 mmol) and 4-N,N-dimethylaminopyridine (10 mg) in dry pyridine (3 ml), and the reaction mixture was left overnight at 20° C. Water (1 ml) was then added, and the resulting mixture was evaporated to dryness. Compound IVb was isolated by flash chromatography (step gradient from 0 to 5% of methanol in dichloromethane in the presence of 0.1% of pyridine) as a pale yellow oil.

The yield of Compound IVb was 0.43 g (62%); $^1$H NMR (CDCl$_3$/CD$_3$OD, 4:1): δ=7.37-6.82, m, 17H, arom.; 6.37, br.s, 1H, NH; 4.55, br.s, 4H, OCOCH$_2$; 3.91, m, 1H, H-2; 3.79, s, 6H, OCH$_3$; 3.53, m, 1H, H-3$_a$; 3.44, m, 1H, H-3$_b$; 3.23, m, 2H, H-1$_{a,b}$; 1.07, s, 9H, CH$_3$. Found: C, 68.53; H, 6.49; N, 1.89. Calculated for C$_{39}$H$_{43}$NO$_{10}$: C, 68.31; H, 6.32; N, 2.04%.

4. Preparation of Support A$_Q$-IV

A mixture of lcaa-CPG (0.3 g), hydroxybenzotriazole (HOBT) (30 mg, 0.2 mmol), N,N'-di-isopropylcarbodiimide (35 µl, 0.2 mmol), and the conjugate of Compound IVa and hydroquinone-O,O'-diacetic acid (i.e., Compound IVb prepared above, 0.15 mmol) in pyridine (5 ml) was agitated overnight at 20° C. The solids were filtered off, washed with pyridine (5 ml), tetrahydrofuran (5 ml), diethyl ether (10 ml), and dried. The resulting support was suspended in a mixture of 1-methylimidazole:tetrahydrofuran (4:21; 5 ml) and acetic anhydride-2,6-lutidine-tetrahydrofuran (1:1:8; 5 ml), agitated for 45 minutes at 20° C., filtered off, washed with tetrahydrofuran (5 ml), acetonitrile (10 ml), diethyl ether (10 ml), and dried. The resulting support A$_Q$-IV contained 40 µmol of DMTr-groups per gram of CPG.

F. Preparation of Support A$_f$

1. Preparation of (±)-3-amino-1-(4,4'-dimethoxytriphenylmethyl)-2-propanediol (Compound V)

Compound Ia (2.5 g, see FIG. 2 and preparation B(2) above) was dissolved in a 9 M solution of ammonia in methanol (75 ml), left overnight at 20° C., and finally evaporated to dryness to produce Compound V, which is illustrated in FIG. 3. This crude Compound V was used for A-support preparation without any additional purification. Crude Compound V: $^1$H NMR (CDCl$_3$): δ=7.88-6.75, m, 13H, arom.; 3.97, m, H-2; 3.78, s, 6H, OCH$_3$; 3.14, m, 2H, J$^3$=5.2, J$^2$=10.1, H-1$_{a,b}$; 3.03, dd, 1H, J$^3$=3.1, J$^2$=12.9, H-3$_a$; 2.91, dd, 1H, J$^3$=8.8, H-3$_b$; 2.35, s, CF$_3$CONH$_2$.

2. Preparation of Support A$_f$

Support A$_f$, as illustrated in FIG. 3, was prepared as follows. A mixture of lcaa-CPG (1 g), succinic anhydride (0.75 g, 7.5 mmol), pyridine (5 ml), and 1-methylimidazole:tetrahydrofuran (4:21; 5 ml) was agitated overnight at 20° C. The solids were filtered off, washed with pyridine (5 ml) and tetrahydrofuran (5 ml). The resulting support was suspended in a mixture of 1-methylimedazole:tetrahydrofuran (4:21; 5 ml) and acetic anhydride-2,6-lutidine-tetrahydrofuran (1:1:8; 5 ml), agitated for 45 minutes at 20° C., filtered off, washed with tetrahydrofuran (5 ml), 10% aqueous pyridine (10 ml), pyridine (5 ml), and acetonitrile (10 ml), and finally dried to give a derivatized controlled pore glass ("CPG") as Compound VI. A mixture of this derivatized CPG, Compound V (1.2 g, 3 mmol), 1-hydroxybenzotriazole (0.46 g, 3 mmol), pyridine (7.5 ml), and N,N'-di-isopropylcarbodiimide (0.47 ml, 3 mmol) was agitated overnight at 20° C. The solids were filtered off, washed with acetonitrile (5 ml), re-suspended in a mixture of triethylamine:water:acetonitrile (1:1:3; 5 ml), agitated for 45 minutes at 20° C., filtered off, washed with acetonitrile (10 ml), and dried to provide Compound VII.

The resulting support (0.42 g of Compound VII) was suspended in a mixture of 2,6-lutidine (3 ml) and tetrahydrofuran (8 ml), and acylated with an acylation mixture (3×0.5 ml over a 3 hour period), prepared from formic acid (1.13 ml, 30 mmol) and acetic anhydride (1.9 ml, 20 mmol). The resulting suspension was agitated overnight at 20° C., filtered off, washed with acetonitrile (10 ml), and finally dried to provide support A$_f$. Support A$_f$ contained 100 µmol of DMTr-groups per gram of CPG.

G. Preparation of Support A$_p$

Support A$_p$, as illustrated in FIG. 3, was prepared as follows. The lcaaCPG, derivatized with succinic anhydride and acetic anhydride (0.42 g of Compound VII), was suspended in a mixture, prepared of phenoxyacetic acid (0.3 g, 2 mmol), N,N'-di-isopropylcarbodiimide (0.312 ml, 2 mmol), pyridine (10 ml), and 4-N,N-dimethyaminopyridine (0.02 g, 0.16 mmol), and agitated overnight at 20° C. The solids were filtered off, washed with acetonitrile (10 ml), and dried to provide support A$_p$. Support A$_p$ contained 100 µmol of DMTr-groups per gram of CPG.

II. Discussion of Oligomer Synthesis and Dephosphorylation

Without limiting this specification or limiting the invention to any particular theory or mechanism of operation, it is believed that the universal supports according to the invention use a mechanism wherein neighboring groups assist in the elimination of the terminal phosphodiester, to thereby generate termini with 3'-hydroxyls. Amides of carboxylic acids may be regarded as weak N—H acids. The amide functional groups will give rise to amide anions in, for example, methanolic ammonia (aqueous methylamine) or ammonium hydroxide. These amide anions, in turn, display basic properties. Therefore, it was believed that, in a basic solution, a vicinal amide group of a 3-acylamido-1,2-propanediol tether could enhance the elimination of terminal phosphodiester along with the linker, which was originally linked to a solid support.

Figure 4:
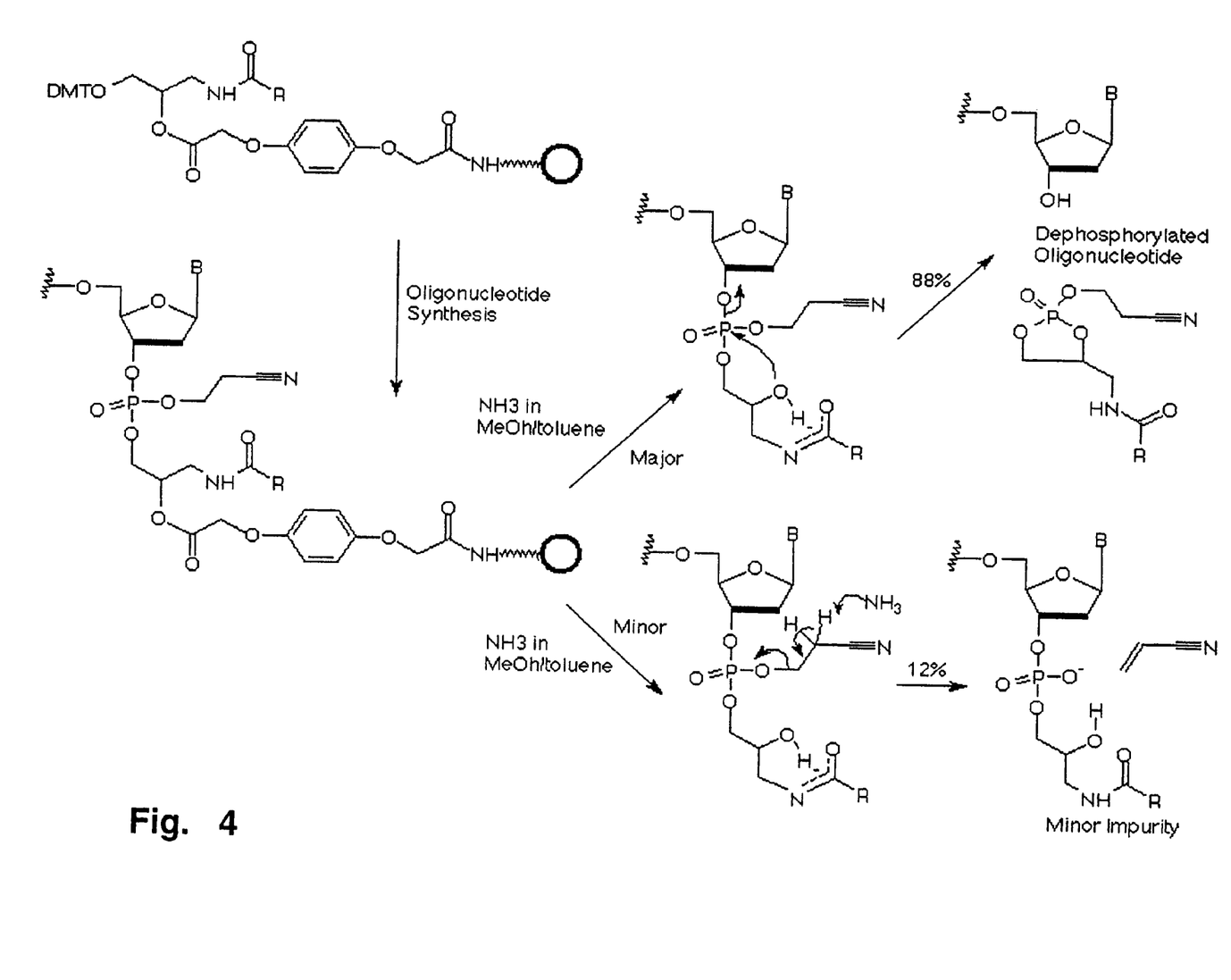
FIG. 4 illustrates a reaction scheme for dephosphorylation and oligomer recovery using supports $A_Q$-I, $A_Q$-II, $A_Q$-III, and $A_Q$-IV for oligomer synthesis.

In order to investigate the usefulness of the $A_Q$ solid supports in the preparation of oligodeoxynucleotides, the short sequence oligo-$T_6$ was assembled on a synthesizer in a conventional manner, using standard phosphoramidite chemistry and recommended protocols. No differences in coupling efficiency (>98% as determined from trityl assay) were detected between the $A_Q$-supports according to the invention and a commercial T-derivatized support. Thus, the $A_Q$-supports were found to be compatible with standard oligomer assembly steps. FIG. 4 illustrates the nucleotide addition to the $A_Q$-support material.

After completion of the oligonucleotide synthesis, addition of ammonia in methanol and toluene rapidly cleaves the hydroquinone-O,O'-diacetate linker and releases the oligomer with a cyanoethyl protected phosphotriester function linked to the 1-hydroxyl of (±)-3-acylamido-1,2-propanediol (FIG. 4). During the subsequent ammonia treatment, the acylamido fragment (in the form of acylamide anion) assists the vicinal 2-hydroxyl group in attacking the phosphorus, giving the desired oligo-$T_6$ and/or 3'-tethered oligomer t-oligo-$T_6$. The investigation of the properties of $A_Q$-supports under various reaction conditions is reported hereafter.

As described above, the assembled sequences were first cleaved from $A_Q$ supports with ammonia in organic solvents. The extent of dephosphorylation and cleavage of the terminal tether was investigated, using ion exchange HPLC. The effect of ammonium hydroxide at 20° C. for 2 hours on the cleavage from a T-bound support also was considered, for comparison purposes. The results of these studies under different conditions and at different temperatures are summarized in Table 1 below.

TABLE 1

Yield of Oligo-$T_6$ derived from the universal solid supports $A_Q$ under various cleavage/elimination conditions.

| Support | Cleavage/elimination mixture | Time | Temperature, ° C. | Yield of oligo-$T_6$, %[a] |
|---|---|---|---|---|
| $A_Q$-I | 9M NH$_3$/MeOH:dioxane (1:1); 32% NH$_3$/H$_2$O | 30 min; 30 min | +20 | 75 |
| $A_Q$-I | 9M NH$_3$/MeOH:dioxane (1:1) | 1 h | +20 | 79 |
| $A_Q$-I | 9M NH$_3$/MeOH:dioxane (1:1) | overnight | +20 | 82 |
| $A_Q$-I | 9M NH$_3$/MeOH:dioxane (1:1) | 2 h | +20 | 80 |
| $A_Q$-I | 9M NH$_3$/MeOH:dioxane (1:1); 32% NH$_3$/H$_2$O | 1 h; 30 min | +4 +20 | 78 |
| $A_Q$-I | 9M NH$_3$/MeOH:dioxane (1:1) | 30 min | +55 | 77 |
| $A_Q$-I | 9M NH$_3$/MeOH:dioxane (1:1) | 30 min | +80 | 76 |
| $A_Q$-I | 9M NH$_3$/MeOH:dioxane (3:2) | 30 min | +80 | 75 |
| $A_Q$-I | 9M NH$_3$/MeOH:dioxane (1:1) | 1 h; 1 h | +4 +20 | 85 |
| $A_Q$-I | 9M NH$_3$/MeOH:dioxane (1:1) | 1 h; 1 h | −20 +20 | 87 |
| $A_Q$-I | 6M NH$_3$ in MeOH—toluene (1:1) | 1 h; 1 h | +4 +20 | 80.6 |
| $A_Q$-I | 5.5M NH$_3$ in MeOH—toluene (1:1) | 1 h; 1 h | +4 +20 | 82.1 |
| $A_Q$-I | 5M NH$_3$ in MeOH—toluene (1:1) | 1 h; 1 h | +4 +20 | 83.0 |
| $A_Q$-I | 4.5M NH$_3$ in MeOH—toluene (1:1) | 1 h; 1 h | +4 +20 | 83.4 |
| $A_Q$-I | 4M NH$_3$ in MeOH—toluene (1:1) | 1 h; 1 h | +4 +20 | 83.6 |
| $A_Q$-I | 3.5M NH$_3$ in MeOH—toluene (1:1) | 1 h; 1 h | +4 +20 | 85.5 |
| $A_Q$-I | 3M NH$_3$ in MeOH—toluene (1:1) | 1 h; 1 h | +4 +20 | 86 |
| $A_Q$-I | 2.5M NH$_3$ in MeOH—toluene (1:1) | 1 h; 1 h | +4 +20 | 87.7 |
| $A_Q$-I | 2M NH$_3$ in MeOH—toluene (1:1) | 1 h; 1 h | +4 +20 | 88.2 |
| $A_Q$-I | 1.5M NH$_3$ in MeOH—toluene (1:1) | 1 h; 1 h | +4 +20 | 87 |
| $A_Q$-III | 9M NH$_3$/MeOH:dioxane (1:1) | 2 h | +20 | 75 |
| $A_Q$-III | 9M NH$_3$/MeOH:dioxane (1:1) | 1 h; 1 h | +4 +20 | 79 |
| $A_Q$-III | 9M NH$_3$/MeOH:dioxane (1:1) | 1 h; 1 h | −20 +20 | 83 |
| $A_Q$-II | 9M NH3/MeOH:dioxane (1:1) | 1 h; 1 h | +4 +20 | 75 |
| $A_Q$-II | 9M NH$_3$/MeOH:dioxane (1:1) | 1 h; 1 h | −20 +20 | 79 |
| $A_Q$-IV | 9M NH$_3$/MeOH:dioxane (1:1) | 1 h; 1 h | −20 +20 | 79 |
| $A_Q$-I | 32% NH$_3$/H$_2$O | 2 h | +20 | 43 |

[a]As assessed from IE HPLC by integration of peaks at 260 nm.

As one can see from the above data, good yields of oligo-$T_6$ (75-88%) were achieved using the $A_Q$-I solid support, incorporating trifluoroacetamido function, and using 2-9 M ammonia in methanol-toluene or methanol-dioxane for cleavage/dephosphorylation. Also, it is noteworthy that under the conditions of ammonium hydroxide cleavage/dephosphorylation, 43% of oligo-$T_6$ was obtained using support $A_Q$-I. While the inventors do not wish to be bound by any particular theory or mechanism, it appears that the presence of water facilitates the competing reaction of β-cyanoethanol elimination (or β-elimination of 2-cyanoethylene), making the use of aqueous ammonia for oligonucleotide cleavage/deprotection less efficient. See FIG. 4, the labeled "minor" product.

From experiments described above, it was concluded that the structure of acylamido function incorporated in the $A_Q$ support does not significantly influence the yield of desired oligo-$T_6$. It was believed that any acylamide anion would assist the vicinal 2-hydroxyl group in attacking the phosphorus. On the other hand, it was concluded that the structure of the linker at the 2-hydroxy group appeared to be important. The cleavage of hydroquinone-O,O'-diacetate group proceeds much faster than the β-elimination of cyanoethyl protecting group. Therefore, the attack of phosphotriester function by the 2-hydroxyl group of 3-acylamido-1,2-propanediol tether takes place, and the desired oligonucleotide was 3'-dephosphorylated.

It was concluded that in a basic solution, the diamide of any dicarboxylic acid (e.g., succinic acid) linking the lcaaCPG and 3-amino-1,2-propanediol tether, should also be capable of assisting the similar attack of 2-hydroxyl group on the phosphorus, provided that this 2-hydroxy function is instantly deprotected with ammonia prior to phosphate deprotection. This attack would then lead to the elimination of the desired oligonucleotide oligo-$T_6$, and the competing reaction would lead to the formation of an lcaaCPG bound oligonucleotide with a phosphodiester group at the 3'-terminus. Considering this reasoning, the two universal A-supports illustrated in FIG. 3 were designed and synthesized. In these supports, the succinyl group bridges the lcaaCPG and 3-amino-1-(4,4'-dimethoxytriphenylmethyl)-2-propanediol via amide bonds, and the 2-hydroxyl function is either formylated ($A_f$) or phenoxyacetylated ($A_p$).

Figure 5:
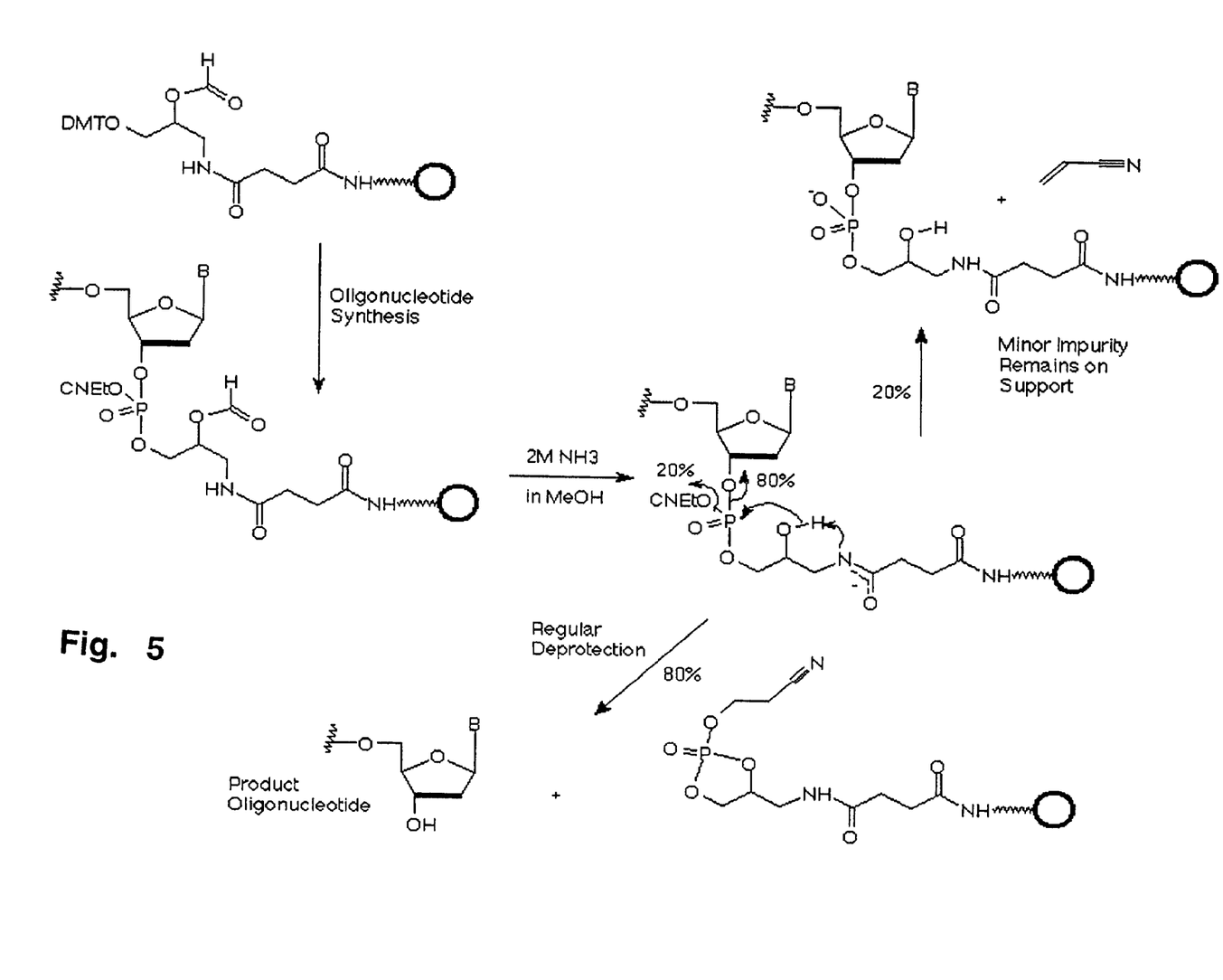
FIG. 5 illustrates a reaction scheme for dephosphorylation and oligomer recovery using supports $A_f$ and $A_p$ for oligomer synthesis.

As in the case of the $A_Q$-supports described above, the short sequence oligo-$T_6$ was assembled on supports $A_f$ and $A_p$, using standard phosphoramidite chemistry and recommended protocols. No differences in coupling efficiency (>98% as determined from trityl assay) were detected between these A-supports and commercial T derivatized supports, which indicated that these A-supports were compatible with standard assembly steps. After completion of the synthesis, addition of ammonia rapidly cleaved the formyl or phenoxyacetyl group and gave the support bound hexamer with a cyanoethyl protected phosphotriester function linked to the 1-hydroxyl of (±)-3-acylamido-1,2-propanediol (see FIG. 5, the "major" product). During the subsequent ammonia treatment, the succindiamido fragment (in the form of a succindiamide anion) assisted the free vicinal 2-hydroxyl group in attacking the phosphorus, thereby releasing the desired oligo-$T_6$ into solution. Unlike the $A_Q$ supports described above, the competing reaction in the case of the $A_f$ and $A_p$ supports led to the formation of lcaaCPG bound oligomer with a phosphodiester group at the 3'-terminus (see the "minor" product branch in FIG. 5). Thus, using the $A_f$ and $A_p$ supports according to the invention, the only oligonucleotide product in the solution appears to be the desired oligonucleotide, along with a small amount of truncated sequences resulting from the non-quantitative coupling steps in the process of oligonucleotide assembly.

The properties of the $A_f$ and $A_p$ supports were investigated under various reaction conditions. First, an assembled oligo-$T_6$ sequence was cleaved from the A-support with ammonia in methanol, and the extent of dephosphorylation/cleavage from the CPG was investigated, using ion exchange HPLC. The optimal conditions of recovery of oligo-$T_6$ from the $A_f$ and $A_p$ supports was assessed from ion exchange HPLC by integration of peaks, corresponding to oligo-$T_6$ (260 nm) derived from 1 µmol of initial solid support. Typically, 0.02 of the total amount of obtained oligomer was injected, and the oligonucleotide peak area was compared to the corresponding area of peak of oligo-$T_6$ resulting from use of a commercial T bound solid support. The results of these studies under different conditions are summarized in Table 2 below:

TABLE 2

Relative yield of oligo-$T_6$ derived from the universal solid supports $A_f$ and $A_p$ under various cleavage/elimination conditions.

| Solid support\conditions for cleavage | Relative of yield[a] oligo-$T_6$, % | Purity, % |
|---|---|---|
| T-support\NH$_3$/H$_2$O, 20° C., 2 h. | 100 | 97 |
| $A_f$-support\ 2 M NH$_3$/MeOH, 20° C., 1 h; NH$_3$/H$_2$O, 20° C., 1 h. | 82 | 96 |
| $A_f$-support\2 M NH$_3$/MeOH, 20° C., 1 h | 77 | 91 (+ about 4% of oligo-$T_6$, containing cyanoethyl protecting groups) |
| $A_f$-support\NH$_3$/H$_2$O, r.t., 1 h. | 42 | 82 (+about 7.8% of unidentified product,) |
| $A_p$-support\ | 29 | 95 |

TABLE 2-continued

Relative yield of oligo-$T_6$ derived from the universal solid supports $A_f$ and $A_p$ under various cleavage/elimination conditions.

| Solid support\conditions for cleavage | Relative of yield[a] oligo-$T_6$, % | Purity, % |
|---|---|---|
| 2 M NH$_3$/MeOH, 20° C., 1 h; NH$_3$/H$_2$O, 20° C., 1 h. | | |

[a]Yield of oligo-$T_6$ resulting from the commercial T bound support was taken as 100%. Relative yield of oligomer, resulting from A-support, was calculated relative to the yield from the T support.

As can be seen, the $A_f$-support particularly leads to high overall yield of the desired oligomer. As in the case with $A_Q$-supports, it is noteworthy that the ammonium hydroxide cleavage/dephosphorylation led to a lower yield of oligo-$T_6$ than methanolic ammonia treatment.

Similar experiments were carried out with a longer sequence oligo-$T_{50}$, assembled on both A-supports and a commercial T-support. In these tests, the crude oligo-$T_{50}$ sample, synthesized on the $A_f$ and $A_p$ supports was treated with 2 M NH$_3$/MeOH (20° C., 1 hour), followed by addition of an equal volume of 32% ammonium hydroxide (20° C., 1 hour). The relative yields of oligo-$T_{50}$, synthesized on different solid supports are summarized in Table 3.

TABLE 3

Relative yield of oligo-$T_{50}$, synthesized on different solid supports. The yield of oligo-$T_{50}$ obtained from the T bound support was taken as 100%.

| Solid support | Relative yield[a] of oligo-$T_{50}$, % |
|---|---|
| $A_f$ | 48 |
| $A_p$ | 17 |
| T | 100 |

[a]Yield of oligo-$T_{50}$ resulting from the commercial T bound support was taken as 100%. Yield of oligomer, resulting from A-support, was calculated relative to the yield from the T-support.

Thus, these preliminary experiments with the $A_f$ and $A_p$ supports demonstrate that the supports may be used as universal solid phase supports, allowing fast and easy cleavage of sufficient amounts of oligonucleotides.

In order to investigate the applicability of supports according to the invention for the preparation of oligodeoxyribonucleotides of mixed sequences, seven longer oligonucleotides were synthesized as follows:

5'-TGGCGTCTTCCATTT-3' (15 mer; SEQ ID NO: 1),

5'-GTGGAATTCCAGCAGCAGAAAGAGCTCATC-3' (30 mer; SEQ ID NO: 2),

5'-TATGGATCCTCAGCTGCAAATGAGG-3' (26 mer; SEQ ID NO: 3),

5'-GTGGAATTCATGAAGAAAGAGATGATCATG-3' (30 mer; SEQ ID NO: 4),

5'-TATGGTACCTCAGCCGTCCGTGCTGCTT-3' (28 mer; SEQ ID NO: 5),

5'-GCGAAGCTTTGGAGAGTGGCATGAAGAAA-3' (29 mer; SEQ ID NO: 6),

5'-TATGGATCCAACCATTCAACATGGTGGAC-3' (29 mer; SEQ ID NO: 7).

The crude 29 mer 5'-GCGAAGCTTTGGAGAGTG-GCATGAAGAAA-3' (SEQ ID NO: 6) above was assembled on an $A_f$-support and cleaved with 2M ammonia in methanol (20° C., 1 hour), and finally deblocked by adding an equal amount of 32% ammonium hydroxide and heating at 55° C.

for an additional 4 hours. The structures of the long oligomers were confirmed by electrospray ionization mass spectra after chromatographic purification.

Also, oligonucleotide phosphorothioate 5'-TGGCGTCT-TCCATTT-3' (SEQ ID NO: 1) was synthesized on a commercial T-bound support and an $A_f$ support following recommended protocols. No differences in coupling efficiency (>98% as determined from trityl assay) were detected between support $A_f$ and the T-support. The support bound oligonucleotide phosphorothioate was cleaved and deblocked as described above and then analyzed by ion exchange HPLC. Analysis of the crude oligonucleotide phosphorothioate prepared on the $A_f$ support indicated that the oligomer prepared on the universal support according to the invention was identical to the phosphoprothioate prepared on a conventional T-bound solid phase.

While the invention has been described in terms of specific examples and embodiments for carrying out the invention, those skilled in the art will appreciate that there are numerous variations and permutations of the above described compositions and methods that fall within the spirit and scope of the invention as set forth in the appended claims.

We claim:

1. A support for oligonucleotide synthesis comprising: a support material represented by the following formula:

wherein substituent A is a member selected from the group consisting of a polymeric base material and a silica base material;
wherein substituent B is a member selected from the group consisting of an acyl group and an aroyl group; and
wherein substituent C is a member selected from the group consisting of a dimethoxytrityl group and a protecting group removable under acidic or neutral conditions.

2. A support according to claim 1, wherein substituent A constitutes a long chain alkylamino controlled pore glass base material.

3. A support according to claim 2, wherein substituent A includes the following substituent:

wherein lcaaCPG and its accompanying substituent groups represent the long chain alkylamino controlled pore glass base material.

4. A support according to claim 2, wherein substituent B is an acyl group.

5. A support according to claim 2, wherein substituent B is a dichloroacetyl group.

6. A support according to claim 2, wherein substituent B is a formyl group.

7. A support according to claim 2, wherein substituent B is a chloroacetyl group.

8. A support according to claim 2, wherein substituent B is a trichloroacetyl group.

9. A support according to claim 2, wherein substituent B is a 4-chlorophenoxyacetyl group.

10. A support according to claim 2, wherein substituent B is a 2,4-dichlorophenoxyacetyl group.

11. An article represented by the following formula:

wherein substituent A is a member selected from the group consisting of a polymeric base material, and a silica base material;
wherein substituent B is a member selected from the group consisting of an acyl group and an aroyl group; and
wherein substituent C is a member selected from the group consisting of a dimethoxytrityl group, a nucleotide-containing group, and a protecting group removable under acidic or neutral conditions.

12. An article according to claim 11, wherein substituent A constitutes a long chain alkylamino controlled pore glass base material.

13. An article according to claim 12, wherein substituent A includes the following substituent:

wherein lcaaCPG and its accompanying substituent groups represent the long chain alkylamino controlled pore glass base material.

14. An article according to claim 12, wherein substituent A includes the following substituent:

wherein Oligoprep 250 and its accompanying substituent groups represent the PVA base material.

15. An article according to claim 12, wherein substituent B is an acyl group.

16. An article according to claim 12, wherein substituent B is a dichioroacetyl group.

17. An article according to claim 12, wherein substituent B is a formyl group.

18. An article according to claim 12, wherein substituent B is a chloroacetyl group.

19. An article according to claim 12, wherein substituent B is a trichioroacetyl group.

20. An article according to claim 12, wherein substituent B is a 4-chiorophenoxyacetyl group.

21. An article according to claim 12, wherein substituent B is a 2,4-dichlorophenoxyacetyl group.

22. An article according to claim 11, represented by the following formula:

wherein lcaaCPG and its accompanying substituent groups represent a long chain alkylamino controlled pore glass base material.

23. An article according to claim 11, represented by the following formula:

wherein lcaaCPG and its accompanying substituent groups represent a long chain alkylamino controlled pore glass base material.

24. An article according to claim 11, wherein substituent C is a nucleotide-containing group including at least one nucleotide selected from the group consisting of: thymidine, 2'-deoxyadenosine, 2'-deoxycytindine, and 2'-deoxyguanosine.

25. An article according to claim 24, wherein the nucleotide-containing group is attached via a phosphotriester group.

26. An article according to claim 11, wherein substituent C is a nucleotide-containing group including a plurality of nucleotides.

27. An article according to claim 11, wherein substituent C is a nucleotide-containing group.

* * * * *

UNITED STATES PATENT AND TRADEMARK OFFICE
CERTIFICATE OF CORRECTION

PATENT NO. : 7,491,817 B2  Page 1 of 1
APPLICATION NO. : 10/851289
DATED : February 17, 2009
INVENTOR(S) : Alex Azhayev et al.

It is certified that error appears in the above-identified patent and that said Letters Patent is hereby corrected as shown below:

In the Claims Section, Column 23, Claim 3, Line 54:
  Please replace "wherein sub stituent A" with --wherein substituent A--.

In the Claims Section, Column 24, Claim 7, Line 39:
  Please replace "a chioroacetyl group" with --a chloroacetyl group--.

In the Claims Section, Column 24, Claim 8, Line 41:
  Please replace "a trichioroacetyl group" with --a trichloroacetyl group--.

In the Claims Section, Column 24, Claim 10, Line 46:
  Please replace "4-dichiorophenoxyacetyl" with --4-dichlorophenoxyacetyl--.

In the Claims Section, Column 25, Claim 16, Line 41:
  Please replace "a dichioroacetyl group" with --a dichloroacetyl group--.

In the Claims Section, Column 25, Claim 19, Line 48:
  Please replace "a trichioroacetyl group" with --a trichloroacetyl group--.

In the Claims Section, Column 25, Claim 20, Line 50:
  Please replace "4-chiorophenoxyacetyl group" with --4-chlorophenoxyacetyl group--.

Signed and Sealed this

Third Day of November, 2009

David J. Kappos
*Director of the United States Patent and Trademark Office*

SEQUENCE LISTING

```
<160> NUMBER OF SEQ ID NOS: 7

<210> SEQ ID NO 1
<211> LENGTH: 15
<212> TYPE: DNA
<213> ORGANISM: Artificial
<220> FEATURE:
<223> OTHER INFORMATION: artificial sequence is an artificially
      synthesized mixed nucleic acid sequence

<400> SEQUENCE: 1
tggcgtcttc cattt                                                    15

<210> SEQ ID NO 2
<211> LENGTH: 30
<212> TYPE: DNA
<213> ORGANISM: Artificial
<220> FEATURE:
<223> OTHER INFORMATION: artificial sequence is an artificially
      synthesized mixed nucleic acid sequence

<400> SEQUENCE: 2
gtggaattcc agcagcagaa agagctcatc                                    30

<210> SEQ ID NO 3
<211> LENGTH: 26
<212> TYPE: DNA
<213> ORGANISM: Artificial
<220> FEATURE:
<223> OTHER INFORMATION: artificial sequence is an artificially
      synthesized mixed nucleic acid sequence

<400> SEQUENCE: 3
tatggatcct cagctgcaaa tgaggg                                        26

<210> SEQ ID NO 4
<211> LENGTH: 30
<212> TYPE: DNA
<213> ORGANISM: Artificial
<220> FEATURE:
<223> OTHER INFORMATION: artificial sequence is an artificially
      synthesized mixed nucleic acid sequence

<400> SEQUENCE: 4
gtggaattca tgaagaaaga gatgatcatg                                    30

<210> SEQ ID NO 5
<211> LENGTH: 28
<212> TYPE: DNA
<213> ORGANISM: Artificial
<220> FEATURE:
<223> OTHER INFORMATION: artificial sequence is an artificially
      synthesized mixed nucleic acid sequence
```

-continued

```
<400> SEQUENCE: 5
tatggtacct cagccgtccg tgctgctt                                    28

<210> SEQ ID NO 6
<211> LENGTH: 29
<212> TYPE: DNA
<213> ORGANISM: Artificial
<220> FEATURE:
<223> OTHER INFORMATION: artificial sequence is an artificially
      synthesized mixed nucleic acid sequence

<400> SEQUENCE: 6
gcgaagcttt ggagagtggc atgaagaaa                                   29

<210> SEQ ID NO 7
<211> LENGTH: 29
<212> TYPE: DNA
<213> ORGANISM: Artificial
<220> FEATURE:
<223> OTHER INFORMATION: artificial sequence is an artificially
      synthesized mixed nucleic acid sequence

<400> SEQUENCE: 7
tatggatcca accattcaac atggtggac                                   29
```